(12) United States Patent
Takiguchi

(10) Patent No.: US 7,892,293 B2
(45) Date of Patent: Feb. 22, 2011

(54) HAIR DYE COMPOSITION

(75) Inventor: Osamu Takiguchi, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/682,613

(22) PCT Filed: Oct. 10, 2008

(86) PCT No.: PCT/JP2008/002885

§ 371 (c)(1),
(2), (4) Date: Apr. 12, 2010

(87) PCT Pub. No.: WO2009/047916

PCT Pub. Date: Apr. 16, 2009

(65) Prior Publication Data

US 2010/0229314 A1    Sep. 16, 2010

(30) Foreign Application Priority Data

Oct. 12, 2007    (JP) ............... 2007-267057

(51) Int. Cl.
*A61Q 5/10*    (2006.01)
(52) U.S. Cl. .................. 8/405; 8/453; 8/455; 8/465; 8/589; 8/676
(58) Field of Classification Search .......... 8/405, 8/453, 455, 465, 589, 676
See application file for complete search history.

(56) References Cited

U.S. PATENT DOCUMENTS

| 4,314,810 A * | 2/1982 | Fourcadier et al. ........... 8/410 |
| 5,798,095 A | 8/1998 | Racky |
| 6,217,855 B1 | 4/2001 | Itou et al. |

FOREIGN PATENT DOCUMENTS

| JP | 4 338316 | 11/1992 |
| JP | 05043425 | 2/1993 |
| JP | 7 330559 | 12/1995 |
| JP | 8 92043 | 4/1996 |
| JP | 9 30937 | 2/1997 |
| JP | 2000 229820 | 8/2000 |
| JP | 2005 179210 | 7/2005 |
| JP | 2006 160641 | 6/2006 |
| JP | 2006 315978 | 11/2006 |
| JP | 2007 63197 | 3/2007 |

OTHER PUBLICATIONS

STIC Search Report dated Sep. 22, 2010.*

* cited by examiner

*Primary Examiner*—Eisa B Elhilo
(74) *Attorney, Agent, or Firm*—Oblon, Spivak, McClelland, Maier & Neustadt, L.L.P.

(57) ABSTRACT

A hair dye composition containing the following components (a) and (b) and having a pH from 2 to 12 at the time of use: (a) 0.1 to 20% by mass of an aromatic sulfone compound represented by the formula (1) shown below:

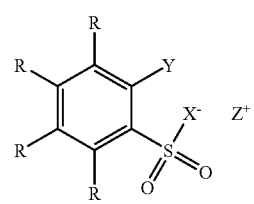

(1)

Wherein R's, Y, $X^-$ and $Z^+$ are defined in the claims and in the disclosure. (b) 0.01 to 5% by mass of at least one component selected from glycylglycine, glycylglycylglycine and salts thereof.

5 Claims, 1 Drawing Sheet

HAIR DYE COMPOSITION

FIELD OF THE INVENTION

The present invention relates to a hair dye composition.

BACKGROUND OF THE INVENTION

In regard to hair dyeing agents, a technology of dyeing hair by subjecting oxidative dye intermediates (precursor and coupler) to an oxidative coupling using an oxidizing agent in the coexistence of an alkali agent, is most commonly used. However, oxidizing agents are prone to cause hair damages, and as a result, damages or weakening of the hair, such as a lift-up or peel-off of cuticles, production of cysteic acid, and reduction of lipids in the hair will occur. These damages or weakening is conspicuous in naturally fine and soft hair, and there is known a problem that when such hair is dyed, the hair lacks bounce, body and volume, and therefore, styling of the hair becomes difficult.

Thus, there have been suggested the following methods which achieve a balance between the dyeing properties and impartation of bounce, body and volume in damaged hair, fragile and weakened hair, or naturally fine and soft hair.

(1) A method of adsorbing a film-forming resin and the like, contained in a hair dye, to the hair surface (Patent Document 1).

(2) A method of using a protein hydrolysate and an amino acid in combination (Patent Document 2).

(3) A method of adding a water-soluble substance to the hair, and forming a substance that is insoluble or poorly soluble in water in the hair (Patent Document 3).

Patent Document 1: JP-A-2000-229820
Patent Document 2: JP-A-H07-330559
Patent Document 3: JP-A-H04-338316

SUMMARY OF THE INVENTION

The present invention provides a hair dye composition containing the following components (a) and (b) and having a pH from 2 to 12 at the time of use:

(a) 0.1 to 20% by mass of an aromatic sulfone compound represented by formula (1) shown below; and (b) 0.01 to 5% by mass of at least one selected from the group consisting of glycylglycine, glycylglycylglycine and salts thereof.

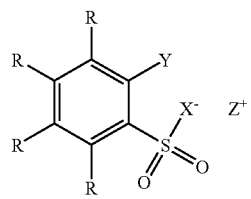

(1)

[wherein R's are identical or different, and each of them represents a hydrogen atom or a monovalent hydrocarbon group, or adjacent two R's are joined to form a saturated or unsaturated bivalent hydrocarbon group; when X is an oxygen atom, Y represents a hydrogen atom, and when X is a nitrogen atom, Y represents a carbonyl group that is bonded to X; and $Z^+$ represents a monovalent cation].

The present invention also provides a method for dyeing hair including applying the hair dye composition to the hair, leaving the hair dye composition to stand for 1 to 60 minutes, and then rinsing the hair dye composition.

DETAILED DESCRIPTION OF THE INVENTION

Figure 1:
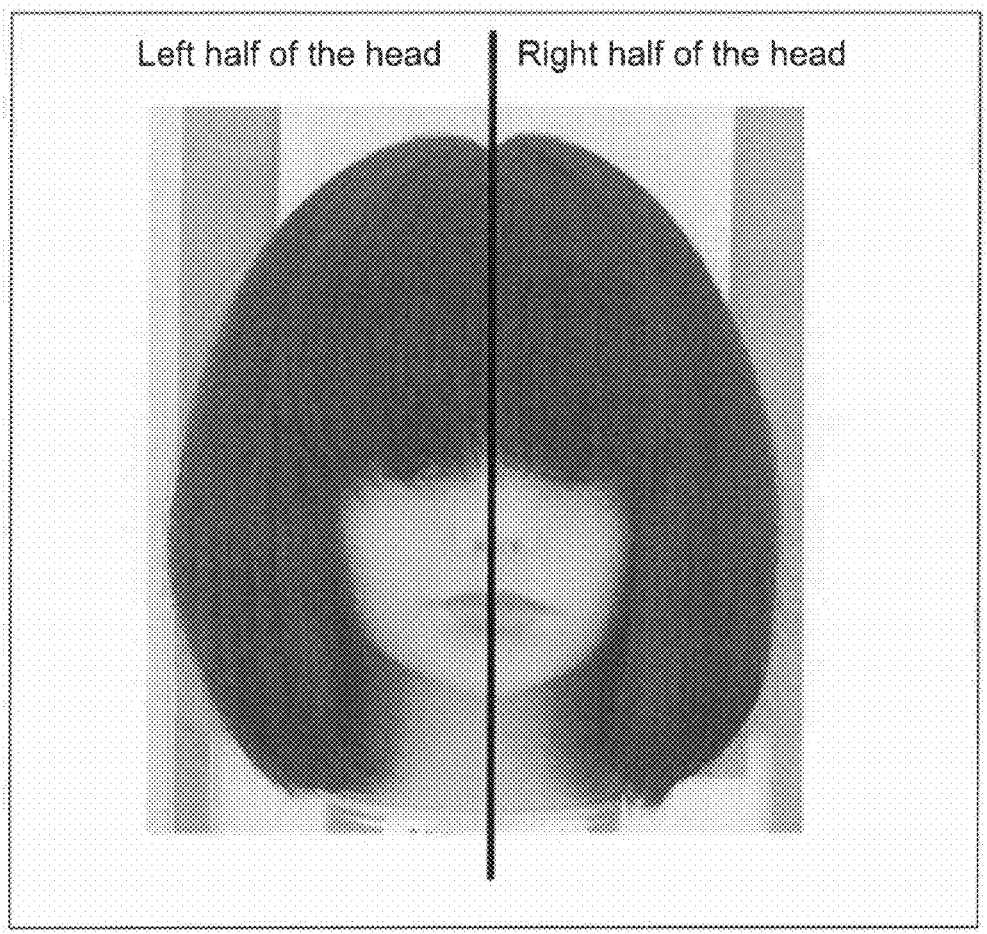
FIG. 1 is a diagram showing the external appearance of a wig before being subjected to a hair dyeing treatment.

The present invention provides a hair dye composition which is excellent in dyeing (or bleaching) ability against damaged hair, fragile or weakened hair, or naturally fine and soft hair, and at the same time, and which can impart bounce, body and volume to the hair; and a method for dyeing the hair using the hair dye composition.

The technologies of the related art as described above all have problems and are not sufficiently satisfactory. That is, the above-mentioned method (1) exhibits its effects when the film-forming resin used and the like adsorb onto the surface of the hair, however, since the film-forming resin and the like fall off from the hair by washing using a shampoo or the like, which process is essential after the hair dyeing treatment, the desired effects are difficult to be manifested. In the above-mentioned method (2), it is considered that various proteins can be used as the raw materials for the protein hydrolysates, but the effects are not constant depending on the type of protein and the lot. Furthermore, in the above-mentioned method (3), although it is possible to impart bounce and body to some extent, the effects were not sufficiently satisfactory for damaged hair, fragile and weakened hair or naturally fine and soft hair.

The inventors of the present invention found that the problems described above may be solved by preparing a hair dye composition containing an aromatic sulfone compound having a specific structure and a specific amino acid in their respective specific amounts.

The hair dye composition of the present invention is excellent in dyeing (or bleaching) ability against damaged hair, fragile and weakened hair or naturally fine and soft hair, and can impart bounce, body and volume to the hair. Furthermore, according to the present invention, a method for dyeing hair, which makes it possible to obtain such effects in a convenient manner is provided.

The hair dye composition of the present invention is a concept which includes both the "one-component type" and the "multi-component type". Here, the term "one-component type" means that the composition is composed of a single agent, and examples of the formulation include:

1) a one-component hair dye composition containing a direct dye and if necessary, an oxidizing agent; and
2) a one-component hair dye composition which contains an oxidizing agent, without containing a dye.

On the other hand, the term "multi-component type" means that the composition is composed of two or more agents, and examples of the formulation include:

3) a two-component hair dye composition which includes a first part containing an alkali agent and a second part containing an oxidizing agent; and
4) a three-component hair dye composition which includes a first part containing an alkali agent, a second part containing an oxidizing agent, and a third part containing an oxidizing aid.

According to the present invention, instances in which an independent agent (hereinafter, referred to as "booster agent") is further combined with any of the formulations described above, shall be included in the relevant formulations. That is, a hair dye composition obtained by further combining a booster agent with a one-component hair dye composition, is defined as a one-component hair dye composition, and a hair dye composition formed by combining a first part containing an alkali agent and a second part containing an oxidizing agent with a booster agent, is defined as a two-component hair dye composition. A hair dye composition formed by combining a first part containing an alkali agent, a second part containing an oxidizing agent, and a third part containing an oxidizing aid with a booster agent, is defined as a three-component hair dye composition.

Such a booster agent may be in the form of, for example, i) a leave-in pre-hair dye treatment agent, which is applied to the hair in advance before a one-component hair dye composition or a mixed liquid of a first part and a second part, and if necessary, a third part, is applied to the hair, and is thereby mixed with the one-component hair dye composition or the mixed liquid on the hair;

ii) a post-hair dye treatment agent which is further applied to the hair after a one-component hair dye composition or a mixed liquid of a first part and a second part, and if necessary, a third part, is applied to the hair, without rinsing the one-component hair dye composition or the mixed liquid, and is thereby mixed with the one-component hair dye composition or the mixed liquid on the hair;

iii) an additive which is further added and mixed with a one-component hair dye composition or a mixed liquid of a first part and a second part, and if necessary, a third part, at the time of preparation. In other words, an agent that is mixed with the one-component hair dye composition or the mixed liquid upon application to the hair, is included in the "booster agent," while an agent that is not mixed with the one-component hair dye composition or the mixed liquid upon application to the hair, is not included in the "booster agent."

The term "hair dye" as used in the present invention is a concept which also includes hair bleach without containing dyes, in addition to hair coloring agents containing dyes. The term "dye(s), dyeing" includes, in regard to a hair dye containing dyes, simply dyeing the hair as well as bleaching and dyeing the hair at the same time, while in regard to a bleach without containing dyes, the term means bleaching the hair. The term "whole composition" as used in the present invention refers to the entire composition used in a hair dyeing treatment including rinsing, and specifically means the mixture obtained after mixing the respective agents constituting the hair dye composition, or a mixture formed by combining the above mixture and a booster agent.

<Component (a)>

The aromatic sulfone compound of the component (a) is a compound represented by the formula (1).

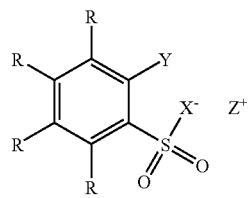

(1)

In the formula (1), R's are identical or different, and each of them represents a hydrogen atom or a monovalent hydrocarbon group, or adjacent two R's are joined to form a saturated or unsaturated bivalent hydrocarbon group. Examples of the monovalent hydrocarbon group include an alkyl group, an aryl group, and an aralkyl group, and an alkyl group having 1 to 8 (preferably 1 to 4) carbon atoms, and an aryl group or aralkyl group having 6 to 10 (preferably 6 to 8) carbon atoms are preferred. Specific examples include a methyl group, an ethyl group, a propyl group, an isopropyl group, a butyl group, a t-butyl group, a phenyl group, a benzyl group, and the like.

Examples of the saturated or unsaturated bivalent hydrocarbon group formed by joining the adjacent two R's include an alkylene group or an alkylidene group, and an alkylene group or alkylidene group having 2 to 6 (preferably 2 to 4) carbon atoms are preferred. Examples thereof include an ethylene group, an ethylidene group, a vinylene group, a trimethylene group, an isopropylidene group, a 1-propenylene group, a tetramethylene group, a 2 methyltrimethylene group, a 1-methyltrimethylene group, a 2-propenylene group, a 2-butenylene group, a buta-1,3-diene-1,4-diyl group, and the like. Specifically, when adjacent two R's are joined to form a buta-1,3-diene-1,4-diyl group, a tetramethylene group, a 1-propenylene group, a 2-propenylene group or a trimethylene group, naphthalenesulfone, tetrahydronaphthalenesulfone, indenesulfone and indanesulfone are respectively formed as the aromatic sulfone, and among them, naphthalenesulfone is preferred.

When X is an oxygen atom, Y represents a hydrogen atom, or when X is a nitrogen atom, Y represents a carbonyl group which is bonded to X. Among them, when X is an oxygen atom, R is preferably an alkyl group, or an alkylidene group formed as adjacent two R's are joined, while when X is a nitrogen atom, R is preferably a hydrogen atom.

The aromatic sulfone compound of the component (a) may have any monovalent cation as the counter-cation $Z^+$, and Z is preferably a hydrogen atom, an alkali metal (for example, a sodium atom or a potassium atom), or ammonium.

More preferred examples of the aromatic sulfone compound of the component (a) include benzenesulfonic acid and/or a salt thereof, para-toluenesulfonic acid and/or a salt thereof, 2,4-dimethylbenzenesulfonic acid and/or a salt thereof, 2,5-dimethylbenzenesulfonic acid and/or a salt thereof, naphthalenesulfonic acid and/or a salt thereof, saccharin and/or a salt thereof, and the like. Among them, para-toluenesulfonic acid and/or a salt thereof, 2,4-dimethylbenzenesulfonic acid and/or a salt thereof, naphthalenesulfonic acid and/or a salt thereof, and saccharin and/or a salt thereof are more preferred. These may be used alone or in combination of two or more.

The component (a) may be incorporated into any one or more parts among the first part, the second part and the third part, or may also be incorporated into the booster agent.

The content of the component (a) is 0.1 to 20% by mass based on the whole composition from the viewpoint of the feel to the touch received from the composition during the procedure and storage stability of the composition, preferably 0.5 to 10% by mass, and more preferably 1 to 7% by mass.

<Component (b)>

The component (b) is at least one selected from glycylglycine, glycylglycylglycine, and salts thereof, and these structure may be a free-form or a zwitterion. Examples of the salts include an inorganic acid salt such as a hydrochloric acid salt and a sulfuric acid salt; an organic acid salt such as a lactic acid salt; an ammonium salt such as an ammonium salt and an alkylammonium salt; an alkali metal salt such as a sodium salt, and the like.

Furthermore, the component (b) may be incorporated into any one of the first part, the second part and the third part, or may be incorporated into the booster agent.

The content of the component (b) is 0.01 to 5% by mass based on the whole composition from the viewpoint of the feel to the touch received from the composition during the procedure and storage stability of the composition, preferably 0.05 to 3% by mass, and more preferably 0.1 to 2% by mass.

The mixing ratio of the component (a) and the component (b) ((a)/(b)) is preferably 1 to 20, more preferably 2 to 15, and even more preferably 2 to 12, by mass, from the viewpoint of suppressing changes in a color tone and further enhancement of the dyeing properties, and certainly imparting a volume-up effect.

The total content of the component (a) and the component (b) is preferably 1 to 10% by mass, more preferably 2 to 9% by mass, and even more preferably 3 to 8% by mass, from the same viewpoints as described above.

<Alkali Agent>

The hair dye composition of the present invention may contain an alkali agent. Furthermore, a multi-component hair dye composition may contain the alkali agent in the first part.

Examples of the alkali agent include ammonia and a salt thereof; an alkanolamine such as monoethanolamine, isopropanolamine, 2-amino-2-methylpropanol and 2-aminobutanol, and a salt thereof; an alkanediamine such as 1,3-propanediamine, and a salt thereof; carbonates such as guanidine carbonate, sodium carbonate, potassium carbonate, sodium hydrogen carbonate and potassium hydrogen carbonate; and the like. Among them, ammonia, alkanolamines and salts thereof are more preferred.

These alkali agents may be used in combination of two or more. The content of the alkali agent is preferably 0.05 to 15% by mass, more preferably 0.1 to 10% by mass, and even more preferably 0.2 to 5% by mass, based on the whole composition, from the viewpoint of obtaining sufficient dyeing properties and bleaching properties, and from the viewpoint of reducing hair damages or scalp stimulation.

<Oxidizing Agent>

The hair dye composition of the present invention may contain an oxidizing agent. Furthermore, a multi-component hair dye composition may contain the oxidizing agent in the second part.

Examples of the oxidizing agent include hydrogen peroxide, hydrogen peroxide or oxygen generating agents such as urea peroxide, melamine peroxide, sodium perborate, potassium perborate, sodium percarbonate and potassium percarbonate. Hydrogen peroxide is more preferred.

The oxidizing agents may be used alone or in combination of two or more. The content of the oxidizing agent is preferably 0.1 to 12% by mass, more preferably 0.5 to 9% by mass, and even more preferably 1 to 6% by mass, based on the whole composition, from the viewpoint of obtaining sufficient hair dyeing/bleaching effects, and from the viewpoint of reducing hair damages or scalp stimulation.

<Oxidizing Aid>

The multi-component hair dye composition of the present invention may contain an oxidizing aid in the third part.

As the oxidizing aid, oxidizing agents other than the oxidizing agents mentioned above may be used, and for example, persulfuric acid salts and the like may be included. Specific examples include ammonium persulfate, potassium persulfate, sodium persulfate, and the like, and these are preferably in the form of powder such as granules.

The oxidizing aids may be used alone or in combination of two or more. The content of the oxidizing aid is preferably 0.1 to 50% by mass, more preferably 1 to 30% by mass, and even more preferably 3 to 25% by mass, based on the whole composition, from the viewpoint of obtaining sufficient bleaching effects, and from the viewpoint of reducing hair damages or scalp stimulation.

[Other Components]

The hair dye composition of the present invention may contain a direct dye. A multi-component hair dye composition may contain a direct dye and/or an oxidation dye intermediate in the first part.

Examples of the direct dye include acid dyes, nitro dyes, disperse dyes, basic dyes, the direct dyes described in JP-A-2003-342139, and the like.

Examples of the acid dyes include Blue No. 1, Violet No. 401, Black No. 401, Orange No. 205, Red No. 227, Red No. 106, Yellow No. 203, Acidic Orange No. 3, and the like.

Examples of the nitro dyes include 2-nitro-para-phenylenediamine, 2-amino-6-chloro-4-nitrophenol, 3-nitro-p-hydroxyethylaminophenol, 4-nitro-ortho-phenylenediamine, 4-amino-3-nitrophenol, 4-hydroxypropylamino-3-nitrophenol, HC Blue No. 2, HC Orange No. 1, HC Red No. 1, HC Yellow No. 2, HC Yellow No. 4, HC Yellow No. 5, HC Red No. 3, N,N-bis(2-hydroxyethyl)-2-nitro-para-phenylenediamine, and the like.

Examples of the disperse dyes include Disperse Violet No. 1, Disperse Blue No. 1, Disperse Black No. 9, and the like.

Examples of the basic dyes include Basic Blue No. 99, Basic Brown No. 16, Basic Brown No. 17, Basic Ted No. 76, Basic Red No. 51, Basic Yellow No. 57, Basic Yellow No. 87, Basic Orange No. 31, and the like.

The direct dyes may be used in combination of two or more, and may also be used in combination with oxidation dye intermediates. The content of the direct dye is preferably 0.001 to 5% by mass, and more preferably 0.01 to 3% by mass, based on the whole composition.

As the oxidation dye intermediates, known precursors and couplers, commonly used in hair dyes, may be used.

Examples of the precursors include para-phenylenediamine, toluene-2,5-diamine, ortho-chloro-para-phenylenediamine, N-phenyl-para-phenylenediamine, N,N-bis(hydroxyethyl)-para-phenylenediamine, 3-methyl-4-aminophenol, 2-hydroxyethyl-para-phenylenediamine, para-aminophenol, para-methylaminophenol, 4-amino-meta-cresol, ortho-aminophenol, salts of these, and the like.

Examples of the couplers include resorcin, 2-methylresorcin, 1-naphthol, 1,5-dihydroxynaphthalene, 5-amino-ortho-cresol, meta-phenylenediamine, meta-aminophenol, 2,4-diaminophenoxyethanol, 2,6-diaminopyridine, 2-methyl-5-hydroxyethylaminophenol, 2-amino-3-hydroxypyridine, salts of these, and the like.

The precursors and couplers may be respectively used alone or in combination of two or more. Their contents are respectively preferably 0.01 to 5%, by mass, and more preferably 0.1 to 4% by mass, based on the whole composition.

The hair dye composition of the present invention may contain a surfactant.

As the surfactant, a cationic surfactant, a nonionic surfactant, an amphoteric surfactant and an anionic surfactant may all be used.

The cationic surfactant is preferably, for example, a mono-long-chain alkyl quaternary ammonium salt. Specific examples include cetrimonium chloride, steartrimonium chloride, behentrimonium chloride, stearalkonium chloride, benzalkonium chloride, and the like, and steartrimonium chloride and behentrimonium chloride are more preferred.

Examples of the nonionic surfactant include polyoxyalkylene alkyl ether, polyoxyalkylene alkenyl ether, higher fatty acid sucrose ester, polyglycerin fatty acid ester, higher fatty acid mono- or diethanolamide, polyoxyethylene hydrogenated castor oil, polyoxyethylene sorbitan fatty acid ester, polyoxyethylene sorbite fatty acid ester, alkylsaccharide, alkylamine oxide, alkylamidoamine oxide, and the like. Among these, polyoxyalkylene alkyl ether and polyoxyethylene hydrogenated castor oil are preferred, and polyoxyethylene alkyl (C12-14) ether is more preferred.

Examples of the amphoteric surfactant include imidazoline, carbobetaine, amidobetaine, sulfobetaine, hydroxysulfobetaine, amidosulfobetaine, and the like.

Examples of the anionic surfactant include alkyl benzenesulfonate, alkyl or alkenyl ether sulfate, alkyl or alkenyl sulfate, olefin sulfonate, alkanesulfonate, saturated or unsaturated fatty acid salts, alkyl or alkenyl ether carboxylate, α-sulfone fatty acid salts, N-acylamino acid, phosphoric acid mono- or diester, sulfosuccinic acid ester, and the like. Examples of alkyl ether sulfate include polyoxyethylene alkyl ether sulfate. Examples of the counterion of the anionic group of these anionic surfactants include alkali metal ions such as sodium ion and potassium ion; alkaline earth metal ions such as calcium ion and magnesium ion; ammonium ion; and alkanolamine having one to three alkanol groups, each having 2 or 3 carbon atoms (for example, monoethanolamine, diethanolamine, triethanolamine, triisopropanolamine, and the like).

The content of the surfactant is preferably 0.1 to 30% by mass, and more preferably 0.5 to 20% by mass, based on the whole composition, from the viewpoint of the emulsifying performance.

The hair dye composition of the present invention may contain a cationic polymer.

The cationic polymer refers to a polymer having a cationic group or a group that can be ionized into a cationic group, and also includes amphoteric polymers which are cationic on the whole. That is, examples of the cationic polymer include a water-soluble polymer containing an amino group or an ammonium group in a side chain of the polymer chain, or a water-soluble polymer containing a diallyl quaternary ammonium salt as a constituent unit. Specific examples include cationized celluloses, cationic starch, cationized guar gum, polymers or copolymers of diallyl quaternary ammonium salts, quaternized polyvinylpyrrolidone, and the like. Among these, polymers containing a diallyl quaternary ammonium salt as a constituent unit, quaternized polyvinylpyrrolidone and cationized celluloses are preferred from the viewpoint of their effects on softness, smoothness and easy finger-combing during shampooing, and easy manageability and moisture retention during drying, and stability of the agent, and polymers or copolymers of diallyl quaternary ammonium salts, and cationized celluloses are more preferred.

Specific examples of the cationic polymer include dimethyldiallylammonium chloride polymers (polyquaternium-6, for example, Merquat 100; Nalco Company), dimethyldiallylammonium chloride/acrylic acid copolymers (polyquaternium-22, for example, Merquat 280 and Merquat 295; Nalco Company), dimethyldiallylammonium chloride/acrylamide copolymers (polyquaternium-7, for example, Merquat 550; Nalco Company), quaternized polyvinylpyrrolidone (Gafquat 734, Gafquat 755 and Gafquat 755N; ISP Japan Ltd.), cationized celluloses (Reogard G and Reogard GP; Lion Corp., Polymer JR-125, Polymer JR-400, Polymer JR-30M, Polymer LR-400, and Polymer LR-30M; Union Carbide Corp.), and the like.

These cationic polymers may be used in combination or two or more. The content of the cationic polymer is preferably 0.001 to 20% by mass, more preferably 0.01 to 10% by mass, and even more preferably 0.05 to 5% by mass, based on the whole composition, from the viewpoints of providing touch enhancing effect and stability of the composition.

The hair dye composition of the present invention preferably contains silicone, so as to impart excellent sense of use.

Examples of the silicone include polysiloxanes, modified silicones (for example, amino-modified silicones, fluorine-modified silicones, alcohol-modified silicones, polyether-modified silicones, epoxy-modified silicones, alkyl-modified silicones, and the like), and cyclic polysiloxanes. Among them, polysiloxanes and amino-modified silicones are preferred, and the examples include BY11-026, BY22-19, FZ-3125, SH200-1,000,000 cs (Dow Corning Toray Co., Ltd.), TSF451-100MA (Momentive Performance Materials Japan Inc.) [all being polysiloxanes]; TSF4440 (Momentive Performance Materials Japan Inc.), KF-6005, KF-6011 (Shin-Etsu Chemical Co., Ltd.) [all being polyether-modified silicones]; SF8451C, SF8452C, SF8457C, SM8704C, SM8904 (Dow Corning Toray Inc.), KF-867 (Shin-Etsu Chemical Co., Ltd.) [all being amino-modified silicones]; and the like may be mentioned.

The content of the silicone is preferably 0.02 to 40% by mass, more preferably 0.1 to 20% by mass, and even more preferably 0.2 to 15% by mass, based on the whole composition, from the viewpoint of providing sufficient effects and suppressing stickiness.

The hair dye composition of the present invention may contain a higher alcohol, from the viewpoint of improving the feel to the touch of the hair and the storage stability of the composition. The higher alcohol can form a structure with the surfactant, to thereby prevent separation of the hair dye composition as well as to improve the feel to the touch during rinsing.

The higher alcohol is preferably an alcohol having 8 to 22 carbon atoms, and more preferably 16 to 22 carbon atoms. Specific examples include cetanol, stearyl alcohol, behenyl alcohol, and the like, and mixtures of these.

The higher alcohols may be used in combination of two or more. The content thereof is preferably 0.01 to 20% by mass, and more preferably 0.1 to 10% by mass, based on the whole composition.

In the hair dye composition of the present invention, water, and if necessary, an organic solvent are used as media.

Examples of the organic solvent include lower alkanols such as ethanol and 2-propanol; aromatic alcohols such as benzyl alcohol and benzyloxyethanol; polyols such as propylene glycol, 1,3-butanediol, diethylene glycol and glycerin; cellosolves such as ethylcellosolve and butylcellosolve; and carbitols such as ethylcarbitol and butylcarbitol.

Other components that are conventionally used as cosmetic raw materials can be added to the hair dye composition of the present invention, in addition to the components described above. Examples of these optional components include hydrocarbons, animal and plant oils and fats, higher fatty acids, natural or synthetic polymeric ethers, antiseptics, chelating agents, stabilizers, antioxidants, plant extracts, crude drug extracts, vitamins, fragrances, ultraviolet absorbents, and the like.

The pH range of the hair dye composition of the present invention at 25° C. may be 2 to 12 during use (during mixing), preferably 3 to 11, from the viewpoint of dyeing and bleaching effects and skin irritancy.

As a pH adjusting agent, a hydroxide such as sodium hydroxide or potassium hydroxide; an inorganic acid such as hydrochloric acid or phosphoric acid; an organic acid such as citric acid, glycolic acid or lactic acid; a hydrochloric acid salt such as hydrochloric acid monoethanolamine; a phosphoric acid salt such as monopotassium dihydrogen phosphate or disodium monohydrogen phosphate can be used, in addition to the alkali agent mentioned above. The pH of the first part before mixing is preferably 8 to 12, and the pH of the second part before mixing is preferably 2 to 5.

The dosage form of the respective agents constituting the hair dye composition of the present invention can be in the form of, for example, solution, emulsion, cream, gel, paste, mousse, aerosol.

The hair dye composition of the present invention preferably has a viscosity that is difficult to drip when the respective agents constituting the hair dye composition are mixed and applied to the hair. For example, the viscosity of the whole composition measured at 25° C. with a helical stand-equipped type B rotary viscometer (type B8R viscometer, Tokimec, Inc.), is preferably 2000 to 100,000 mPa·s. Herein, the viscosity is defined as the value obtained after rotating the composition for one minute at 10 rpm using a Rotor T-C.

The hair dye composition of the present invention is, for example, applied to the hair after the respective agents constituting the hair dye composition (including the booster agent previously described) are mixed at the time of use. The treatment method includes, for example, a method of applying the composition to the hair, subsequently leaving the composition to stand for a predetermined time, rinsing and drying the composition. The temperature for application to the hair is preferably 15 to 45° C., and the time for application is preferably 1 to 60 minutes. In this case, the hair dye composition may be lightly rinsed with water, and then the hair may be washed using a shampoo containing an anionic surfactant, and subsequently washed with water. When the hair dye composition contains a cationic polymer and a silicone, the cationic polymer appropriately flows out, while the silicone appropriately remains on the hair, so that satisfactory conditioning effects can be imparted. The shampoo is preferably a common aqueous shampoo containing about 5 to 20% by mass of an anionic surfactant such as sodium lauryl sulfate, sodium laureth-1 sulfate, sodium laureth-2 sulfate or sodium laureth-3 sulfate.

EXAMPLES

Examples 1 to 6 and Comparative Examples 1 to 5

First parts A1 to A6 and B1 to B5 shown in Table 1 were respectively prepared. These first parts were respectively mixed with a second part X1 shown in Table 2 at a mass ratio of 9:1, to obtain hair dye compositions of Examples 1 to 6 and Comparative Examples 1 to 5, respectively. Furthermore, this treatment caused bleaching of the hair.

[1: Degree of Upstanding]

The hair dye compositions of Examples 1 to 6 and Comparative Examples 1 to 5 were used to evaluate the shaping and the degree of upstanding according to the following procedure.

<1-1: Shaping and Measurement of Height of Upstanding (Before Treatment)>

10 strands of Caucasian hair (manufactured by Kerling International Haarfabrik GmbH) having an average minor axis of 47 to 54 μm were cut to a length of 10 cm, and were immersed in ion-exchanged water for 3 hours. Subsequently, while the ten strands were gathered into one tress and maintained straight, the hair tress was left to dry for 24 hours in a constant temperature constant humidity chamber at room temperature of 20° C. and a relative humidity of 65%, to perform shaping into a straight form. After the shaping, one strand out of the ten was taken out inside the same constant temperature constant humidity chamber, the ends of the hair were maintained perpendicular with forceps, and the height of upstanding was measured. Similarly, the height of upstanding was measured for the remaining 9 strands, and an average value, x, of the ten strands was determined.

<1-2: Hair Dyeing Process>

The ten strands, for which x was measured as described in section <1-1>, were fixed at their one ends to the gathered part of 1 g of a tress of Caucasian hair provided separately. This 1 g of hair tress to which the ten strands of hair were fixed, was coated with 1 g of the hair dye composition of Example 1. The hair tress was left to stand for 20 minutes at 30° C., and then was rinsed with water at about 40° C. The hair tress was washed with a shampoo for evaluation as shown in Table 3 and was washed with water.

<1-3: Shaping and Measurement of Height of Upstanding (after Treatment)>

The ten strands of hair, for which x was measured in section <1-1>, were removed from the hair tress that had been subjected to the treatment of <1-2>. Subsequently, the ten strands were gathered into one tress and maintained straight, the hair tress was left to dry for 24 hours in a constant temperature constant humidity chamber at room temperature of 20° C. and a relative humidity of 65%, to perform shaping into a straight form. After the shaping, one strand out of the ten was taken out inside the same constant temperature constant humidity chamber, the ends of the hair were maintained perpendicular with forceps, and the height of upstanding was measured. Similarly, the height of upstanding was measured for the remaining 9 strands, and an average value, x', of the ten strands was determined.

<1-4: Evaluation of Upstanding>

From a ratio of x and x', the degree of upstanding, y=x'/x, was determined. That is, a larger value of y means that the volume-up effect is greater.

TABLE 1

| | First part- A1 to A6, B1 to B5 | | | | | | | | | | |
|---|---|---|---|---|---|---|---|---|---|---|---|
| | Example | | | | | | Comparative Example | | | | |
| Component (mass %) | 1 A1 | 2 A2 | 3 A3 | 4 A4 | 5 A5 | 6 A6 | 1 B1 | 2 B2 | 3 B3 | 4 B4 | 5 B5 |
| p-toluenesulfonic acid | — | — | — | 2.20 | 5.60 | — | — | — | — | — | — |
| Sodium p-toluenesulfonate | 3.80 | — | — | — | — | — | 3.80 | — | 3.80 | — | — |
| Sodium naphthalenesulfonate | — | 3.30 | — | — | — | — | — | — | — | — | — |
| Sodium 2,4-dimethylbenzenesulfonate | — | — | 3.80 | — | — | — | — | — | — | — | — |
| Sodium saccharin | — | — | — | — | — | 3.30 | — | — | — | — | — |

TABLE 1-continued

First part- A1 to A6, B1 to B5

| | Example | | | | | | Comparative Example | | | | |
|---|---|---|---|---|---|---|---|---|---|---|---|
| Component (mass %) | 1<br>A1 | 2<br>A2 | 3<br>A3 | 4<br>A4 | 5<br>A5 | 6<br>A6 | 1<br>B1 | 2<br>B2 | 3<br>B3 | 4<br>B4 | 5<br>B5 |
| Taurine | — | — | — | — | — | — | — | — | — | 3.30 | — |
| Sodium lauryl sulfonate | — | — | — | — | — | — | — | — | — | — | 3.30 |
| Glycylglycylglycine | — | 0.56 | — | — | — | — | — | — | — | — | — |
| Glycylglycine | 0.56 | — | 0.56 | 1.10 | 0.56 | 1.10 | — | 0.56 | — | 0.56 | 0.56 |
| Aspartame | — | — | — | — | — | — | — | — | 1.10 | — | — |
| sodium hydroxide aqueous solution (48 mass %) | — | — | — | 1.06 | 2.70 | — | — | — | — | — | — |
| Aqueous ammonia (28 mass %) | 3.30 | 3.30 | 3.30 | 3.30 | 3.30 | 3.30 | 3.30 | 3.30 | 3.30 | 3.30 | 3.30 |
| Purified water | Balance | Balance | Balance | Balance | Balance | Balance | Balance | Balance | Balance | Balance | Balance |
| Total | 100 | 100 | 100 | 100 | 100 | 100 | 100 | 100 | 100 | 100 | 100 |
| pH (25° C.) after mixing of first part and second part | 9.7 | 9.7 | 9.7 | 9.6 | 9.7 | 9.6 | 9.8 | 9.7 | 9.8 | 9.7 | 9.7 |
| Degree of upstanding y | 1.12 | 1.10 | 1.11 | 1.07 | 1.13 | 1.11 | 0.98 | 0.99 | 1.04 | 0.96 | 1.04 |

TABLE 2

Second part X1

| Component (mass %) | Second part X1 |
|---|---|
| Aqueous hydrogen peroxide (35 mass %) | 100 |

From the results of Table 1, in the hair dyeing treatment based on Example 1 and the hair dyeing treatment based on Comparative Example 1, the difference in the degree of upstanding, y, is 0.14. This difference in the degree of upstanding of 0.14 is a value that allows sensing of an obvious difference in volume, as it can be seen from the sensory evaluation of volume 1 described later.

[2: Evaluation of Volume at Head Top of Wig]

Figure 2:
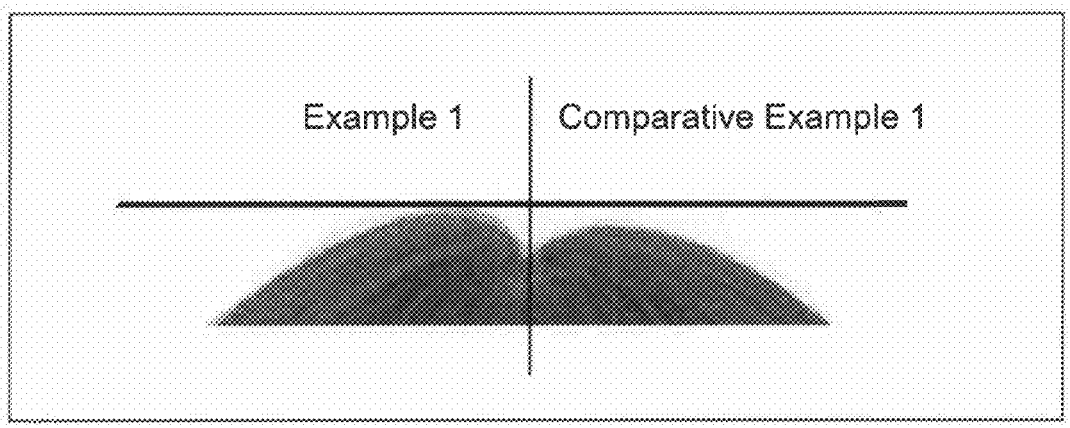
FIG. 2 is a magnified view of the top of the head of the wig after finishing.

40 g of the hair dye composition of Example 1 was applied to the hair at the left half of the head, as viewed from the front side, of a Chinese hair wig as shown in FIG. 1 (manufactured by Beaulax Co., Ltd.), and 40 g of the hair dye composition of Comparative Example 1 was applied to the hair at the right half of the head as viewed from the front side. The wig was left to stand for 20 minutes at room temperature, and then was rinsed with water at about 40° C. The wig was washed with the shampoo for evaluation shown in Table 3 and was washed with water. Subsequently, a hairdresser blow-dried (warm hair at about 80° C.) the wig equally on the right and the left using a roll brush (V-roll C-508 manufactured by Takigawa Co., Ltd.), to finish up. A magnified view of the top of the head of the wig after finishing is shown in FIG. 2.

TABLE 3

Shampoo for evaluation

| Component (mass %) | Shampoo for evaluation |
|---|---|
| Sodium laureth-1 sulfate | 15.00 |
| EDTA-2Na | 0.10 |
| Phosphoric acid*[1] | q.s. |
| Purified water | Balance |
| Total | 100 |

*[1]Amount to adjust the pH to 7

From FIG. 2, it can be seen that the hair at the left top of the head which had been subjected to hair dyeing with the hair dye composition of Example 1, has more volume as compared with the right top of the head which had been subjected to hair dyeing with the hair dye composition of Comparative Example 1.

[3: Sensory Evaluation of Volume 1]

The hair volume of the wig which had been subjected to the "evaluation of volume at head top of wig" as described above, was subjected to a sensory evaluation by five evaluators according to the following criteria. In this sensory evaluation of volume, in addition to the extent of volume of the hair in terms of the look of the top or temporal region of the head, the bounce and firmness upon actual touch with a hand were also added to rate the volume sensory score. The score distribution for the sensory evaluation of volume is presented in Table 4.

<Evaluation Scores>

Score 5: The hair on the side applied with the hair dye composition of Example 1, obviously has volume.

Score 4: The hair on the side applied with the hair dye composition of Example 1 has volume.

Score 3: Both sides are equal.

Score 2: The hair on the side applied with the hair dye composition of Comparative Example 1 has volume.

Score 1: The hair on the side applied with the hair dye composition of Comparative Example 1, obviously has volume.

TABLE 4

| Sensory evaluation of volume | Score distribution for sensory evaluation of volume (number of persons) | | | | |
|---|---|---|---|---|---|
| | Score 5 | Score 4 | Score 3 | Score 2 | Score 1 |
| Example 1 versus Comparative Example 1 | 3 | 2 | 0 | 0 | 0 |

It is clear from Table 4 that the hair dyed with the hair dye composition of Example 1 is felt more voluminous than the hair dyed with the hair dye composition of Comparative Example 1.

[4: Sensory Evaluation of Volume 2]

Furthermore, Example 4 and Comparative Example 3, which constitutes a combination of hair dye compositions having the closest values of the degree of hair upstanding, y, among the hair dye compositions of the Examples and the hair dye compositions of the Comparative Examples described in Table 1, were subjected to the same evaluation as the sensory evaluation of volume 1. That is, the same sensory evaluation of volume was performed using Example 4 instead of Example 1 and using Comparative Example 3 instead of Comparative Example 1. The score distribution for the sensory evaluation of volume is presented in Table 5.

<Evaluation Score>

Score 5: The hair on the side applied with the hair dye composition of Example 4, obviously has volume.

Score 4: The hair on the side applied with the hair dye composition of Example 4 has volume.

Score 3: Both sides are equal.

Score 2: The hair on the side applied with the hair dye composition of Comparative Example 3 has volume.

Score 1: The hair on the side applied with the hair dye composition of Comparative Example 3, obviously has volume.

TABLE 5

| Sensory evaluation of | Score distribution for sensory evaluation of volume (number of persons) | | | | |
|---|---|---|---|---|---|
| volume 2 | Score 5 | Score 4 | Score 3 | Score 2 | Score 1 |
| Example 4 versus Comparative Example 3 | 2 | 3 | 0 | 0 | 0 |

Among the measurement results for the degree of upstanding shown in Table 1, the difference between Example 4 and Comparative Example 3 or Comparative Example 5 was the smallest, which was 0.03. As it can be seen from the sensory evaluation of volume 2, the hair dye treatment based on Example 4 obviously imparts more volume as compared with the hair dye treatment based on Comparative Example 3.

Therefore, even if the difference of the degree of upstanding, y, is only 0.03, the difference in volume can be clearly recognized.

Example 7, Comparative Example 6

Two-Component Hair Dye Composition

First parts A7 and B6 shown in Table 6 and a second part X2 shown in Table 7 were respectively prepared. As shown in Table 8, these first parts were respectively mixed with the second part X2 at a mass ratio of 1:1, to obtain hair dye compositions of Example 7 and Comparative Example 6, respectively. The pH (at 25° C.) obtained after mixing the first part and the second part was 9.4 and 9.6, respectively. Evaluations of the degree of upstanding, dyeing properties and the feel to the touch of the hair after dyeing, were carried out by the following evaluation methods.

TABLE 6

First part A7, B6

| | First part | |
|---|---|---|
| Component (mass %) | A7 | B6 |
| Sodium p-toluenesulfonate | 6.70 | — |
| Glycylglycine | 1.00 | — |
| Toluene-2,5-diamine | 1.00 | 1.00 |
| 5-Amino-ortho-cresol | 0.02 | 0.02 |
| Meta-aminophenol | 0.12 | 0.12 |
| Para-aminophenol | 0.58 | 0.58 |
| Resorcin | 0.47 | 0.47 |
| Cetearyl alcohol | 10.80 | 10.8 |
| Cocamide MEA | 4.60 | 4.60 |
| Oleth-5 | 5.00 | 5.00 |
| Oleic acid | 2.50 | 2.50 |
| Propylene glycol | 1.00 | 1.00 |
| Sodium lauryl sulfate | 1.70 | 1.70 |
| EDTA-4Na | 0.20 | 0.20 |
| Ammonium chloride | 0.50 | 0.50 |
| Anhydrous sodium sulfite | 1.00 | 1.00 |
| Ascorbic acid | 0.50 | 0.50 |
| D-pantothenyl alcohol | 0.25 | 0.25 |
| Aqueous ammonia (28 mass %) | 8.20 | 8.20 |
| Purified water | Balance | Balance |
| Total | 100 | 100 |

TABLE 7

Second part X2

| Component (mass %) | Second part X2 |
|---|---|
| EDTA-4Na | 0.05 |
| Salicylic acid | 0.01 |
| Disodium hydrogen phosphate | 0.11 |
| Sodium lauryl sulfate | 0.19 |
| Phosphoric acid | 0.404 |
| D-pantothenyl alcohol | 0.25 |
| Cetearyl alcohol | 1.71 |
| Aqueous hydrogen peroxide (35 mass %) | 6.00 |
| Purified water | Balance |
| Total | 100 |

[5: Degree of Upstanding]

For each of the hair dye compositions of Example 7 and Comparative Example 6, the heights of upstanding before and after the hair dyeing treatment, x and x', were measured by the procedure described in the section [1: Degree of upstanding], and the degree of upstanding, y=x'/x, was determined. The degree of upstanding, y, is presented together in Table 8.

[6: Evaluation of Dyeing Properties]

The color tint of 1 g of a tress of Chinese white hair (manufactured by Beaulax Co., Ltd.) was measured with the CIE color coordinate system ($L^*_1$, $a^*_1$, $b^*_1$) using a colorimeter (Chroma meter CR-400 manufactured by Konica Minolta Sensing, Inc.). Ten sets of this hair tress (total 10 g) were applied with 10 g of the hair dye composition of Example 7. The hair tresses were left to stand for 20 minutes at 30° C., and then were rinsed with water at about 40° C. The hair tresses were cleansed with a shampoo for evaluation shown in Table 3, and then were washed with water. Subsequently, the color tint of the hair tress after the hair dyeing treatment was measured again for 1 g each of the hair tress, with the CIE color coordinate system ($L^*_2$, $a^*_2$, $b^*_2$) using the colorimeter. $\Delta E^*$ was calculated for 1 g each of the hair tress by the following mathematical formula, and an average value for the ten sets was determined. A larger value of $\Delta E^*$ means more excellent dyeing properties. For Comparative Example 6, ΔE* was also determined in the same manner. The results for the evaluation of dyeing properties are presented together in Table 8.

$$\Delta E^* = \sqrt{(L_2^* - L_1^*)^2 + (a_2^* - a_1^*)^2 + (b_2^* - b_1^*)^2} \quad \text{[Mathematical formula 1]}$$

TABLE 8

|  | Mixing ratio (mass ratio) | Example 7 | Comparative Example 6 |
|---|---|---|---|
| First part | 1 | A7 | B6 |
| Second part | 1 | X2 | |
| pH after mixing first part and second part (25° C.) | | 9.4 | 9.6 |
| Degree of upstanding, y | | 1.06 | 1.01 |
| Dyeing properties ΔE* | | 51.2 | 51.5 |

[7: Evaluation of Feel to the Touch of Hair 1]

For two monitors having short hair, with the length of the hair at the top of the head being about 15 cm, the hair dye composition of Example 7 was applied to the left half of the head of each monitor, and the hair dye composition of Comparative Example 6 was applied to the right half of the head of each monitor, as shown in FIG. 1. The hair was left to stand for 20 minutes at room temperature, and then was rinsed with water at about 40° C. The hair was washed with the shampoo for evaluation shown in Table 3, and was washed with water. Subsequently, a hairdresser dried the hair equally on the right side and the left side by blow-drying (warm air at about 80° C.) to finish up.

It was confirmed by the hairdresser that in all of the monitors, the hair dye composition of Example 7 imparted bounce and body to the hair, as compared with the hair dye composition of Comparative Example 6.

Example 8 and Comparative Example 7

One-Component Hair Dye Composition Used in Combination with Booster Agent

Booster agents Z1 and Z0 shown in Table 9, and a second part X3 shown in Table 10 were respectively prepared. As shown in Table 11, these booster agents Z1 and Z0 were respectively mixed with the second part X3 at a mass ratio of 9:1, to obtain hair dye compositions of Example 8 and Comparative Example 7, respectively. The pH (25° C.) obtained after mixing the booster agent and the second part was 3.1 in both cases. An evaluation of the degree of upstanding was carried out according to the following procedure. Furthermore, this treatment caused bleaching of the hair.

TABLE 9

Booster agent Z0 to Z2

|  | Booster agent | | |
|---|---|---|---|
| Component (mass %) | Z0 | Z1 | Z2 |
| Sodium p-toluenesulfonate | | 3.8 | 34.0 |
| Glycylglycine | | 0.5 | 10 |

TABLE 9-continued

Booster agent Z0 to Z2

|  | Booster agent | | |
|---|---|---|---|
| Component (mass %) | Z0 | Z1 | Z2 |
| Sodium hydroxide aqueous solution (48 mass %) *2 | | q.s. | q.s. |
| Purified water | 100 | Balance | Balance |
| Total | 100 | 100 | 100 |

*2 Amount to adjust the pH to 7

TABLE 10

Second part X3

| Component (mass %) | Second part X3 |
|---|---|
| 35% Aqueous hydrogen peroxide | 37.1 |
| Disodium hydrogen phosphate | 0.5 |
| Phosphoric acid*3 | q.s. |
| Purified water | Balance |
| Total | 100 |

*3 Amount to adjust the pH to 3.1

[8: Degree of Upstanding]

For each of the hair dye compositions of Example 8 and Comparative Example 7, the heights of upstanding before and after the hair dyeing treatment, x and x', were measured by the procedure described in the section [1: Degree of upstanding], and the degree of upstanding, y=x'/x, was determined. The degree of upstanding, y, is presented together in Table 11.

TABLE 11

|  | Mixing ratio (mass ratio) | Example 8 | Comparative Example 7 |
|---|---|---|---|
| Booster agent | 9 | Z1 | Z0 |
| Second part | 1 | X3 | |
| pH after mixing booster agent and second part (25° C.) | | 3.1 | 3.1 |
| Degree of upstanding y | | 1.06 | 1.02 |

As it can be seen from the results shown in Table 11, the hair dye composition of the present invention according to Example 8 enhanced the upstanding of each strand of the hair, and thus exhibited a volume-up effect.

Example 9 and Comparative Example 8

Two-Component Hair Dye Composition Used in Combination with Booster Agent

Booster agents Z2 and Z0 shown in Table 9, a first part B7 shown in Table 12, and a second part X4 shown in Table 13 were respectively prepared. As shown in Table 14, these booster agents Z2 and Z0 were respectively mixed with the first part B7 and the second part X4 at a mass ratio of 1:4.5:4.5, to obtain hair dye compositions of Example 9 and Comparative Example 8, respectively. The pH (25° C.) obtained after mixing the booster agent, the first part and second part was 6.8 in both cases. For these hair dye compositions, evaluations of the degree of upstanding and dyeing properties were carried out according to the procedures described in the sections [1: Degree of upstanding] and [6: Evaluation of dyeing properties]. The results are presented together in Table 14.

TABLE 12

| Component (mass %) | First part B7 |
|---|---|
| Toluene-2,5-diamine | 1.00 |
| 5-Amino-ortho-cresol | 0.04 |
| Meta-aminophenol | 0.05 |
| 2-Amino-3-hydroxypyridine | 0.045 |
| Resorcin | 0.32 |
| Cetearyl alcohol | 9.00 |
| Cocamide MEA | 3.20 |
| Oleth-5 | 0.60 |
| Oleic acid | 1.00 |
| Sodium lauryl sulfate | 1.00 |
| EDTA-4Na | 0.20 |
| Ammonium chloride | 0.25 |
| Anhydrous sodium sulfite | 0.25 |
| Ascorbic acid | 0.20 |
| D-pantothenyl alcohol | 0.30 |
| Methylparaben | 0.001 |
| Phenoxyethanol | 0.002 |
| Sodium benzoate | 0.002 |
| Purified water | Balance |
| Total | 100 |

TABLE 13

| Component (mass %) | Second part X4 |
|---|---|
| 35% Aqueous hydrogen peroxide | 5.71 |
| EDTA-4Na | 0.06 |
| Salicylic acid | 0.01 |
| Disodium hydrogen phosphate | 0.10 |
| Sodium lauryl sulfate | 0.39 |
| Purified water | Balance |
| Total | 100 |

TABLE 14

| | Mixing ratio (mass ratio) | Example 9 | Comparative Example 8 |
|---|---|---|---|
| Booster agent | 1 | Z2 | Z0 |
| First part | 4.5 | B7 | B7 |
| Second part | 4.5 | X4 | X4 |
| pH after mixing booster agent, first part and second part (25° C.) | | 6.8 | 6.8 |
| Degree of upstanding y | | 1.10 | 1.01 |
| Dyeing properties ΔE* | | 18.3 | 18.0 |

The hair dye composition of the present invention enhanced the upstanding of each strand of the hair while imparting equal dyeing properties, and thus imparted a volume-up effect.

Formulation Example 1

A first part shown in Table 15 and the second part X2 shown in Table 7 can be mixed at a mass ratio of 1:1 and then applied to the hair.

TABLE 15

| Component (mass %) | First part |
|---|---|
| Sodium p-toluenesulfonate | 3.8 |
| Glycylglycine | 0.56 |
| Toluene-2,5-diamine | 0.45 |
| 5-Amino-ortho-cresol | 0.10 |
| Meta-aminophenol | 0.18 |
| Para-aminophenol | 0.74 |
| Resocinol | 0.62 |
| Ortho-aminophenol | 0.10 |
| Cetearyl alcohol | 10.8 |
| Cocamide MEA | 4.6 |
| Oleth-5 | 5 |
| Oleic acid | 2.5 |
| Propylene glycol | 1.0 |
| Sodium lauryl sulfate | 1.7 |
| EDTA-4Na | 0.2 |
| Ammonium chloride | 0.5 |
| Anhydrous sodium sulfite | 1.0 |
| Ascorbic acid | 0.5 |
| Polysilicone-9 | 0.15 |
| Aqueous ammonia (28 mass %) | 8.2 |
| Purified water | Balance |
| Total | 100.0 |

Formulation Example 2

Three-Component Hair Dye Composition

The first part A7 shown in Table 6, the second part X2 shown in Table 7, and a third part Y shown in Table 16 are mixed at a mass ratio of 1:1:0.3 to 1, and the mixture is applied to the hair.

TABLE 16

| Component (mass %) | Third part Y |
|---|---|
| Sodium persulfate | 10.00 |
| Potassium persulfate | 16.00 |
| Ammonium persulfate | 26.00 |
| Anhydrous sodium metasilicate | 20.00 |
| Sodium silicate | 17.80 |
| Silicic anhydride | 1.00 |
| Sodium stearate | 5.00 |
| Sodium lauryl sulfate | 1.00 |
| Anhydrous tetrasodium edetate | 1.00 |
| β-Cyclodextrin | 0.20 |
| Xanthan gum | 1.00 |
| Carboxymethylcellulose sodium | 1.00 |
| Total | 100 |

Formulation Example 3

A first part shown in Table 17, the second part X2 shown in Table 7, and a booster agent Z3 shown in Table 18 can be mixed at a mass ratio of 5:5:1 and then applied to the hair.

TABLE 17

| Component (mass %) | First part |
|---|---|
| Toluene-2,5-diamine | 0.45 |
| 5-Amino-ortho-cresol | 0.10 |

TABLE 17-continued

| Component (mass %) | First part |
|---|---|
| Meta-aminophenol | 0.18 |
| Para-aminophenol | 0.74 |
| Resorcinol | 0.62 |
| Ortho-aminophenol | 0.10 |
| Cetearyl alcohol | 10.8 |
| Cocamide MEA | 4.6 |
| Oleth-5 | 5 |
| Oleic acid | 2.5 |
| Propylene glycol | 1.0 |
| Sodium lauryl sulfate | 1.7 |
| EDTA-4Na | 0.2 |
| Ammonium chloride | 0.5 |
| Anhydrous sodium sulfite | 1.0 |
| Ascorbic acid | 0.5 |
| Polysilicone-9 | 0.15 |
| Aqueous ammonia (28 mass %) | 8.2 |
| Purified water | Balance |
| Total | 100 |

TABLE 18

Booster agent Z3

| Component (mass %) | Booster agent Z3 |
|---|---|
| Sodium para-toluenesulfonate | 30 |
| Glycylglycine | 10 |
| Purified water | 60 |
| Total | 100 |

Formulation Example 4

A commercially available two-component hair dye composition (for example, Blaune Cream Hair Color manufactured by Kao Corp.) is purchased, and the hair dye composition can be mixed with the booster agent Z3 shown in Table 18 at a mass ratio of 10:1 and then applied to the hair.

Formulation Example 5

One-Component Hair Dye Composition

A one-component hair dye composition shown in Table 19 is prepared and applied to the hair.

TABLE 19

| Component (mass %) | Formulation Example 5 |
|---|---|
| Sodium p-toluenesulfonate | 3.40 |
| Glycylglycine | 1.00 |
| Orange No. 205 | 0.48 |
| Black No. 401 | 0.28 |
| Violet No. 401 | 0.03 |
| Red No. 227 | 0.04 |
| Glycolic acid aqueous solution (71 mass %) | 4.00 |
| Ethanol | 10.00 |
| Benzyloxyethanol | 10.00 |
| Glycerin | 2.00 |
| (C12-14) Pareth-9 | 0.24 |
| PEG-9 dimethicone*[4] | 0.80 |
| PEG-11 methyl ether dimethicone*[5] | 0.80 |

TABLE 19-continued

| Component (mass %) | Formulation Example 5 |
|---|---|
| Hydroxypropylxanthan gum*[6] | 1.40 |
| Sodium hydroxide aqueous solution (48 mass %)*[7] | q.s. |
| Perfume | 0.16 |
| Purified water | Balance |
| Total | 100 |

*[4]KF-6005, Shin-Etsu Chemical Co., Ltd.
*[5]KF-6011, Shin-Etsu Chemical Co., Ltd.
*[6]Rhaball Gum EX, Dainippon Sumitomo Pharma Co., Ltd.
*[7]Amount to adjust the pH to 3

Formulation 6 One-Component Hair Dye Composition

A one-component hair dye composition shown in Table 20 is prepared and applied to the hair.

TABLE 20

| Component (mass %) | Formulation Example 6 |
|---|---|
| Sodium p-toluenesulfonate | 3.40 |
| Glycylglycine | 1.00 |
| Basic Brown No. 16 | 0.30 |
| HC Yellow No. 2 | 0.20 |
| HC Yellow No. 4 | 0.30 |
| Basic Red No. 76 | 0.60 |
| Basic Blue No. 99 | 0.10 |
| Aqueous ammonia (28 mass %) | 8.00 |
| Isopropyl alcohol | 3.50 |
| Laureth-23 | 0.50 |
| Benzyl alcohol | 8.00 |
| Oleic acid | 7.50 |
| LPG (4.0 kg/cm$^2$) | 10.00 |
| Ammonium chloride*[8] | q.s. |
| Purified water | Balance |
| Total | 100 |

*[8]Amount to adjust the pH to 10

The invention claimed is:

1. A hair dye composition comprising the following components (a) and (b) and having a pH from 2 to 12 at the time of use:

(a) 0.1 to 20% by mass of an aromatic sulfone compound represented by the following formula (1):

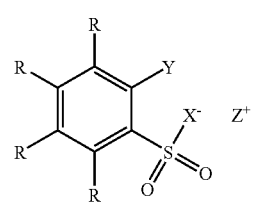

(1)

wherein R's are identical or different, and each of them represents a hydrogen atom or a monovalent hydrocarbon group, or adjacent two R's are joined to form a saturated or unsaturated bivalent hydrocarbon group; when X is an oxygen atom, Y represents a hydrogen atom, and when X is a nitrogen atom, Y represents a carbonyl group that is bonded to X; and Z$^+$ represents a monovalent cation; and (b) 0.01 to 5% by mass of at least one component selected from the group consisting of glycylglycine, glycylglycylglycine and salts thereof.

2. The hair dye composition according to claim 1, wherein the total content of the components (a) and (b) is 1 to 10% by mass.

3. The hair dye composition according to claim 1 or 2, wherein the component (a) is at least one selected from the group consisting of para-toluenesulfonic acid, 2,4-dimethylbenzenesulfonic acid, naphthalenesulfonic acid, saccharin and salts of these.

4. The hair dye composition according to claim 1, further comprising an oxidizing agent as a component (c).

5. A method for dyeing hair, comprising applying the hair dye composition according to claim 1 to the hair and leaving the hair dye composition to stand for 1 to 60 minutes and then rinsing the hair dye composition.

* * * * *